US011717680B2

(12) United States Patent
Bullock et al.

(10) Patent No.: US 11,717,680 B2
(45) Date of Patent: Aug. 8, 2023

(54) CRANIAL PROSTHETIC

(71) Applicant: QV Bioelectronics Ltd., Nether Alderley (GB)

(72) Inventors: Christopher John Bullock, Nether Alderley (GB); Richard Zhiming Fu, Nether Alderley (GB); Hani Joseph Marcus, London (GB); Carl Albert Stone, Manchester (GB)

(73) Assignee: QV Bioelectronics Ltd., Nether Alderley (GB)

( * ) Notice: Subject to any disclaimer, the term of this patent is extended or adjusted under 35 U.S.C. 154(b) by 0 days.

(21) Appl. No.: 17/653,593

(22) Filed: Mar. 4, 2022

(65) Prior Publication Data

US 2022/0280786 A1    Sep. 8, 2022

(30) Foreign Application Priority Data

Mar. 5, 2021   (GB) ..................... 2103110

(51) Int. Cl.
*A61N 1/36*    (2006.01)
*A61N 1/04*    (2006.01)

(52) U.S. Cl.
CPC ....... *A61N 1/36002* (2017.08); *A61N 1/0476* (2013.01); *A61N 1/0492* (2013.01)

(58) Field of Classification Search
CPC ............. A61N 1/36002; A61N 1/0476; A61N 1/0492; A61N 1/36025; A61N 1/0526;
(Continued)

(56) References Cited

U.S. PATENT DOCUMENTS 6,978,180 B2    12/2005 Tadlock
7,096,070 B1    8/2006  Jenkins et al.
(Continued)

FOREIGN PATENT DOCUMENTS

WO    WO-2008087489 A8    11/2008
WO    WO-2016179712 A1    11/2016
(Continued)

OTHER PUBLICATIONS

"United Kingdom Application GB2103110.9, Combined Search and Examination Report dated Jul. 22, 2021", (Jul. 22, 2021), 3 pgs.
(Continued)

*Primary Examiner* — Carl H Layno
*Assistant Examiner* — Anh-Khoa N Dinh
(74) *Attorney, Agent, or Firm* — Schwegman Lundberg & Woessner, P.A.

(57) ABSTRACT

A cranial prosthetic comprises a perforated plate, wherein the perforations comprise a plurality of holes substantially equidistant from a central point. One such cranial prosthetic comprises a curved perforated plate, wherein the perforations comprise four holes substantially equidistant from a central point. In an example, the perforated plate also comprises an additional hole at the central point, detachable screw/suture fixing tabs for attaching the cranial prosthetic to the cranium via screws/sutures, detachable securing means consisting of flaps that secure the electrode when closed, and indentations in the form of channels suitable for recessing extension leads with at least one exit point, which connect individual electrodes to the main lead. Removable protective caps may be placed over the detachable securing means when closed.

17 Claims, 7 Drawing Sheets

(58) Field of Classification Search
CPC .. A61N 1/0531; A61N 1/0534; A61N 1/3605; A61N 1/0539; A61F 2/2875; A61F 2230/0006; A61F 2/28; A61F 2/30965; A61F 2002/30143; A61F 2002/30462; A61F 2002/3092; A61F 2002/30578; A61F 2002/4638; B33Y 80/00; A61M 2025/105; A61M 25/10; A61M 2025/024; A61M 2025/028; A61M 2210/0687; A61M 25/02; A61B 2562/0215; A61B 5/25; A61B 17/0057; A61B 2090/103; A61B 90/10; A61H 23/02; A61H 39/002; A61H 39/04

See application file for complete search history.

(56) References Cited

U.S. PATENT DOCUMENTS

| | | | |
|---|---|---|---|
| 7,283,856 | B2 | 10/2007 | Boling |
| 8,032,231 | B1 | 10/2011 | Gilson et al. |
| 8,718,778 | B2 | 5/2014 | Bikson et al. |
| 9,101,756 | B1* | 8/2015 | Pianca ............... A61N 1/0539 |
| 9,155,889 | B2 | 10/2015 | Hershey |
| 9,179,875 | B2 | 11/2015 | Hua |
| 2005/0015128 | A1* | 1/2005 | Rezai ................ A61N 1/0539 600/378 |
| 2009/0112327 | A1* | 4/2009 | Lane ................... A61B 90/10 623/16.11 |
| 2010/0280585 | A1* | 11/2010 | Appenrodt ........... A61N 1/0534 607/149 |
| 2011/0092960 | A1* | 4/2011 | Shachar ............ A61M 5/14224 604/891.1 |
| 2011/0112394 | A1 | 5/2011 | Mishelevich |
| 2013/0304216 | A1 | 11/2013 | Paspa et al. |
| 2014/0155859 | A1* | 6/2014 | Bonde ................ A61N 1/0539 604/500 |
| 2014/0257325 | A1 | 9/2014 | Chavez et al. |
| 2014/0288625 | A1* | 9/2014 | Yin .................... A61N 1/0539 607/116 |
| 2017/0266438 | A1 | 9/2017 | Sano et al. |
| 2019/0060637 | A1 | 2/2019 | Duijsens et al. |
| 2019/0282802 | A1 | 9/2019 | Malinowski |
| 2019/0308025 | A1* | 10/2019 | Bauer ................ A61B 17/3468 |
| 2019/0314627 | A1 | 10/2019 | Greenberg et al. |
| 2020/0030099 | A1* | 1/2020 | Sampath ............... A61B 5/686 |

FOREIGN PATENT DOCUMENTS

| | | |
|---|---|---|
| WO | WO-2017039762 A1 | 3/2017 |
| WO | WO-2018005936 A1 | 1/2018 |
| WO | WO-2018072894 A1 | 4/2018 |
| WO | WO-2018119220 A1 | 6/2018 |
| WO | WO-2020018662 A1 | 1/2020 |
| WO | WO-2020047285 A1 | 3/2020 |
| WO | WO-2022184893 | 9/2022 |

OTHER PUBLICATIONS

"United Kingdom Application GB2103110.9, Search Report dated Jul. 21, 2021", (Jul. 21, 2021), 1 pg.

Jiang, Jingle, et al., "A testbed for optimizing electrodes embedded in the skull or in artificial skull replacement pieces used after injury", J Neurosci Methods. Feb. 1, 2017; 277: 21-29. doi:10.1016/j.jneumeth.2016.12.005, (Feb. 1, 2017), 21-29.

Kirson, Eilon D., et al., "Alternating electric fields arrest cell proliferation in animal tumor models and human brain tumors", PNAS; 2007; 104(24):10152-7; doi:10.1073/pnas.0702916104, (Jun. 12, 2007), 10152-7.

Stupp, Roger, et al., "Effect of Tumor-Treating Fields Plus Maintenance Temozolomide vs Maintenance Temozolomide Alone on Survival in Patients With Glioblastoma", JAMA; 2017; 318(23):2306-16; doi: 10.1001/jama.2017.18718, (Dec. 19, 2017), 2306-16.

Toms, S. A., et al., "Increased compliance with tumor treating fields therapy is prognostic for improved survival in the treatment of glioblastoma: a subgroup analysis of the EF-14 phase III trial", Journal of Neuro-Oncology; 2019; 141(2):467-473; doi:10.1007/s11060-018-03057-z, (Dec. 1, 2018), 467-473.

"International Application No. PCT/EP2022/055549, International Search Report and Written Opinion dated Jun. 14, 2022", (Jun. 14, 2022), 12 pgs.

"International Application No. PCT/EP2022/055549, updated Written Opinion dated Oct. 10, 2022", (Oct. 10, 2022), 7 pgs.

"International Application No. PCT/EP2022/055558, response filed Sep. 20, 2022 to Written Opinion of the International Preliminary Examining Authority dated Jun. 14, 2022", (Sep. 20, 2022), 3 pgs.

"International Application No. PCT/EP2022/055549, International Preliminary Report on Patentability dated Mar. 2, 2023", (Mar. 2, 2023), 7 pgs.

"International Application No. PCT/EP2022/055549, Response to Written Opinion", (dated Sep. 20, 2022), 8 pgs.

* cited by examiner

CRANIAL PROSTHETIC

CROSS-REFERENCE TO RELATED APPLICATION

This application claims the benefit of priority under 35 U.S.C. § 119 to Great Britain Patent Application No. GB 2103110.9, entitled "CRANIAL PROSTHETIC," filed on Mar. 5, 2021, the disclosure of which is incorporated by reference herein in its entirety.

FIELD

The present specification relates to a cranial prosthetic. More specifically the present specification relates to a cranial prosthetic, which comprises a perforated plate and indentations suitable for recessing leads, wherein the perforations comprise a plurality of holes substantially equidistant from a central point.

BACKGROUND

Electrotherapy involves the use of electrical energy in medical treatment and can apply to a variety of treatments, including the use of electrical devices such as deep brain stimulators (DBS) for neurological disease such as Parkinson's disease. Electrotherapy can be used as a physical therapy for muscle stimulation, pain management and wound healing for example, but it may also be used for the treatment of psychological symptoms for example anxiety, insomnia, depression, hypervigilance, and obsessive compulsive disease.

Electrotherapy has also been demonstrated to be an effective treatment for glioblastoma multiforme (GBM), the most common type of primary brain tumors in adults. In phase III multi-center clinical trials, electrotherapy has been shown to increase patient overall survival to 21 months when used as an addition to surgery (for example surgical resection), chemotherapy and radiotherapy (Stupp et al.; JAMA; 2017; 318(23):2306-16; doi: 10.1001/jama.2017.18718.). This is achieved by delivering alternating sinusoidal electrical fields at specific frequencies (50-300 kHz) to the head. At these frequencies, electrical fields have been shown to interfere with cancer cell mitosis, thereby slowing the growth of recurrent tumors and extending patient survival (Kirson et al.; PNAS; 2007; 104(24):10152-7; doi:10.1073/pnas.0702916104).

At present, there is only one electrotherapy device in clinical use for cancer treatment. In this device, the therapeutic electrical fields are delivered to the patient's head by the means of transducer arrays affixed to the scalp. These transducers are connected to an external battery and stimulator pack that the patients must carry around with them and the recommended daily treatment period is 18 hours per day. However, there are several problems with this external stimulation approach. Firstly, the electrical fields generated within the brain (where the tumor resection margins are located) are exponentially weaker than those at the skin surface where the electric field is being generated, which limits treatment efficacy. In order to account for this and ensure an electrical field of sufficient effective strength is generated at the treatment site, a large heavy battery is used resulting in a highly cumbersome device which impacts patient independence and mobility. Furthermore, the transducers affixed to the scalp are highly conspicuous, take approximately 50 minutes to apply to the head each morning and require the patient's head to be shaved every two days. This greatly impacts a patient's quality of life, and the continuous placement of the transducers of the scalp can cause severe skin irritation and resultant pain as a consequence of the large electrical currents that are crossing the skin. These impacts on patient's quality of life mean only a small percentage of patients comply with the recommended daily dosing time (Toms et al.; Journal of Neuro-Oncology; 2019; 141(2):467-473; doi:10.1007/s11060-018-03057-z). There is a clear correlation between amount of time each day GBM patients are receiving electrotherapy and overall survival, with the data strongly suggestive that continuous (24 h/day) treatment would result in the greatest overall survival, so the issues with patient compliance is directly limiting the treatment efficacy.

Many challenges of the existing treatment could be overcome by delivery of electrical fields from within the tumor or the tumor resection cavity. This would result in higher electrical field strengths, which should result in improved patient outcomes. Furthermore, this approach would remove the problem of painful skin irritation experienced with the existing device described above (there is no sensation from within brain tissue for example). It would allow for continuous electrotherapy, which could significantly improve patient outcomes. Delivery of electrical fields from within the tumor or the tumor resection cavity would also have benefits for the accompanying device needed to deliver the charge. As a result of the focal application of the electrical fields, an exponentially lower voltage would be required to generate the same electrical field strengths than with the existing device. Use of lower voltages enables the usage of smaller batteries (which last longer), and enables the device to be miniaturized and implanted. By entirely implanting the device, it is possible to overcome several quality of life issues—there is nothing visible outside of the body, nothing cumbersome to carry around, and for brain tumors, no head shaving required.

Deep brain stimulation (DBS) is a neurosurgical procedure involving the placement of a medical device called a neurostimulator, which sends electrical impulses through implanted electrodes to specific targets in the brain. Typically, DBS treatment is delivered by a single implanted electrode, which may have multiple active sites along its axis. DBS has been used for the treatment of movement disorders, including Parkinson's disease, essential tremor, and dystonia. These electrodes can be partially implanted in a patient's brain via a burr hole formed in the patient's cranium, typically formed using a drill fitted with a special drill bit. The electrodes are connected to a charge delivery device via a lead implanted through the burr hole and secured in place via a burr hole cover. Various such systems have been previously described: US2019308025A1 describes a cranial implant for device fixation in burr holes; US2019282802A1 describes kits and methods for securing a burr hole plugs for stimulation systems; US2014257325A1 describes recessed burr hole covers and methods for using the same; and US2013304216A1 describes burr hole covers and methods for using same; however all of these systems describe devices for one single electrode.

JingLe Jiang et al. (J. Neurosci. Methods 2017 Feb. 1; 277: 21-29) describe a testbed for optimizing electrodes embedded in the skull or in artificial skull replacement pieces used after injury. They theorize that chronic brain recordings would beneficial after injury/surgery for monitoring brain health and seizure development and that embedding electrodes directly in these artificial skull replacement pieces would be a novel, low-risk way to perform chronic brain monitoring in these patients. The device described by JingLe Jiang et al. is not used or suitable for supporting an optimal arrangement of electrodes embedded within the brain tissue.

When treating brain tumors, the cancer cells can be located at any point in three-dimensional space within the tumor or tumor resection margins, covering a total volume of tissue far greater in size (in the order of 10 cm$^3$) than the focal tissue regions (<1 cm$^3$) targeted by deep brain stimulation techniques. In order to ensure effective treatment of all of the cancer cells in the tumor or tumor resection margins, it is necessary to generate an electrical field over this relatively large volume of tissue such that the minimum electrical field strength at any spatial point within the 3D volume of the tumor resection margins is sufficient to interfere with cancer cell mitosis, this can be defined as a clinically effective electrical field. Due to the exponential drop off of electrical field strength with increasing distance from a stimulating electrode, generating a large volume clinically effective electrical field is better achieved through the use of multiple electrodes implanted on spatially distant trajectories. By implanting these multiple electrodes along the circumference or periphery of the tumor or tumor resection margins, it is possible to reduce the maximum distance between any point in 3D space within the tumor or resection margins and the nearest implanted electrode. As a result, the minimum electrical field strength within the total volume of the tumor or resection margins will be increased. This in turn will reduce the input voltage required and therefore energy demand to generate a clinically effective electrical field, with resultant benefits to the battery life and total size of a stimulating device. This in turn may enable the complete implantation of the medical device, with resultant benefit to patient quality of life without impacting treatment efficacy.

In addition to ensuring that the electrical field strength is clinically effective, there is also benefit in this electrical field being as near to uniform as possible, where a uniform electrical field is defined as one where the electrical field strength of any point within that field is independent of its position in 3D space. A uniform electrical field will also further reduce the energy demand to generate a clinically effective electrical field, by reducing the regions of the electrical field being over-stimulated above the clinically effective field strength. The uniformity of an electrical field generated by multiple implanted electrodes can be increased by implanting a plurality of electrodes substantially equidistant from a central point. The uniformity of an electrical field generated by multiple implanted electrodes may be further increased by implanting an electrode at the central point. The uniformity of the electrical field may be further increased by implanting more than one plurality of electrodes substantially equidistant from a central point (e.g., in a concentric circular arrangement with an optional electrode at the central point).

WO 2017/039762 describes a low-profile intercranial device for use in surgery, particularly cranioplasty, craniomaxillofacial surgery and neurosurgery, but it does not envisage multi-electrode electrotherapy, nor the associate problems addressed by the cranial prosthetic of the present application. US 2010/0280585 describes a method and apparatus for securing an electrode, particularly a surgical procedure, and particularly to a method and apparatus for securing at least one electrode to an anatomy, such as at least one deep brain stimulator (DBS) electrode, but it does not envisage or address the associated problems of multi-electrode electrotherapy addressed by the cranial prosthetic of the present application.

Electrotherapy involving multiple implanted electrodes in the brain has many advantages over existing electrotherapy treatments, but in order for multiple electrodes to be implanted safely during surgery and firmly held in position, a device is required to secure the electrodes to the skull. The device must be economically compatible with the charge delivery device and be able to accommodate and preferably organize each of the leads connecting the multiple implanted electrodes to the charge delivery device—loose leads after surgical implantation of the device risk skin erosion and wound breakdown. Furthermore, correctly organized leads may assist with protection from induced current during an MRI scan. The device should be able to secure these leads in place whilst reducing irregular protrusion. Since the device is implanted as part of a complex surgical procedure, surgical useability is also important—the harder it is for the surgeons to implant, the longer the surgery will take. Longer surgeries are more dangerous for patients and more expensive for hospital systems. The present application describes a novel cranial prosthetic suitable for use in electrotherapy for treating brain tumors and metastases.

SUMMARY

This specification describes, in part, a cranial prosthetic, which comprises a perforated plate and indentations suitable for recessing leads, wherein the perforations comprise a plurality of holes substantially equidistant from a central point.

This specification also describes, in part, a process for the manufacture of a cranial prosthetic which comprises injection molding, machining, casting or 3D printing the cranial prosthetic.

This specification also describes, in part, a cranial prosthetic for use in electrotherapy.

BRIEF DESCRIPTION OF THE DRAWINGS

The drawings illustrate generally, by way of example, but not by way of limitation, various embodiments discussed in the present document.

DETAILED DESCRIPTION

Figure 1A:
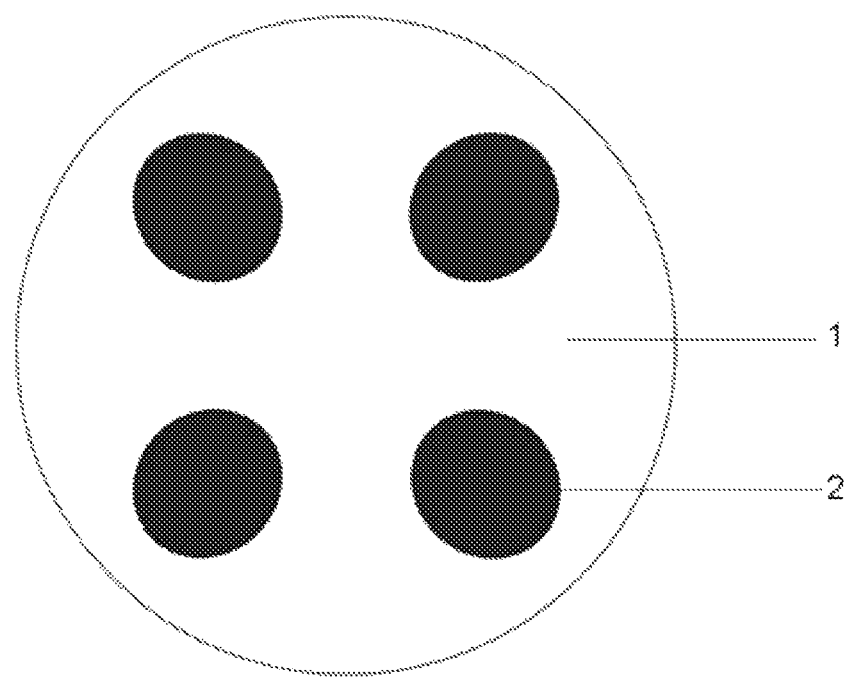
FIG. 1A is a plan view of a cranial prosthetic, which comprises a perforated plate (1), wherein the perforations comprise four holes (2) substantially equidistant from a central point.
Figure 1B:
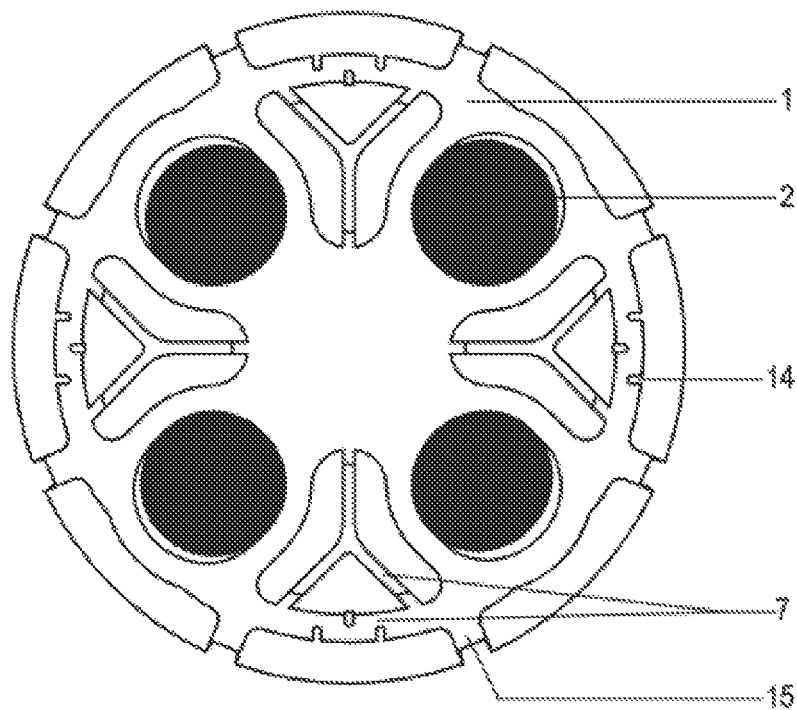
FIG. 1B is a plan view of a cranial prosthetic, which comprises a perforated plate (1), wherein the perforations comprise four holes (2) substantially equidistant from a central point, indentations suitable for recessing leads (7) with at least one exit point (15), and protrusions into the channel (14).
Figure 2A:
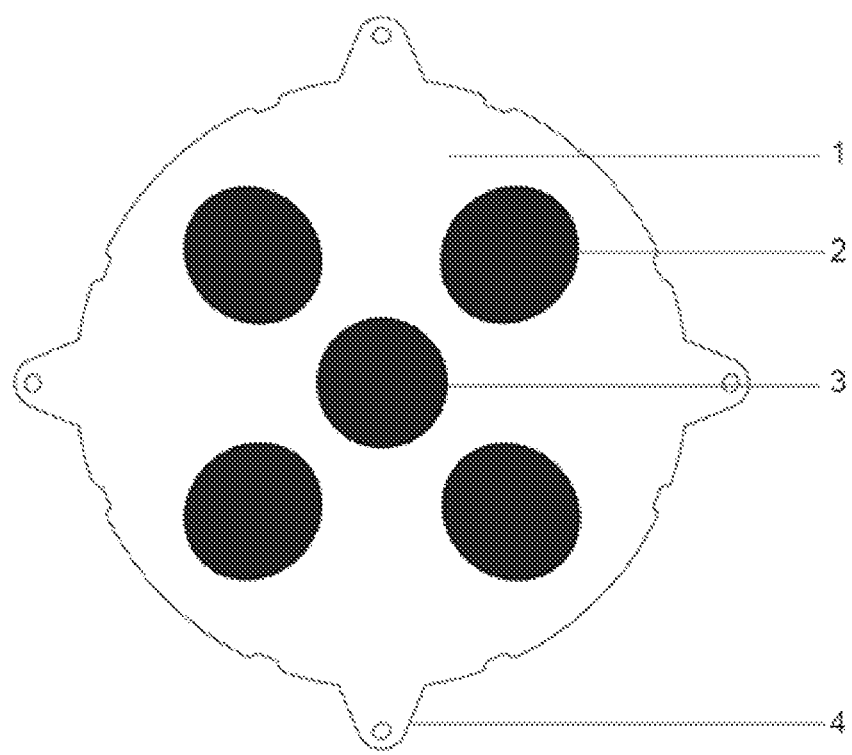
FIG. 2A is a plan view of a cranial prosthetic, which comprises a perforated plate (1), wherein the perforations comprise four holes (2) substantially equidistant from a central point. The plate also comprises an additional hole at the center point (3) and incorporated screw fixing tabs (4) for attaching the cranial prosthetic to the cranium via screws.
Figure 2B:
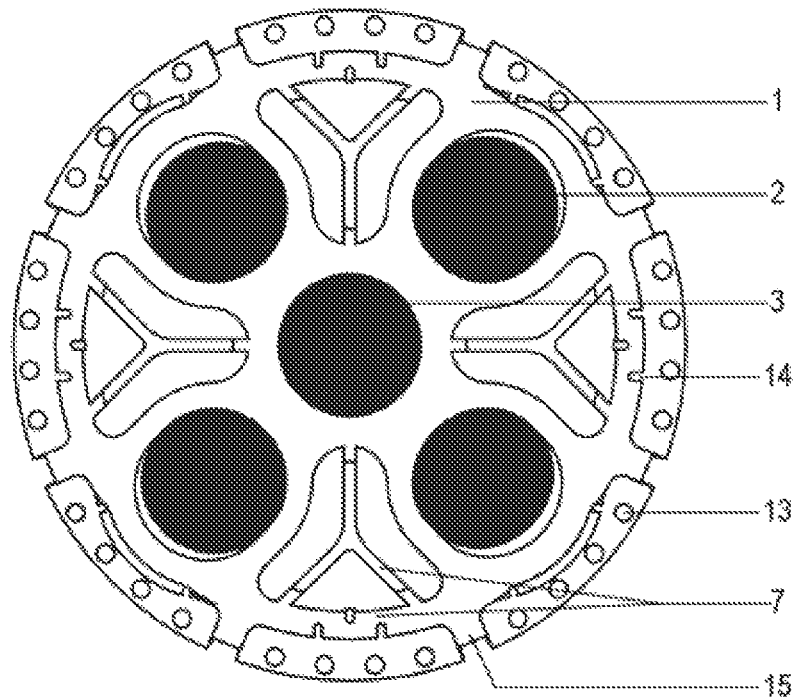
FIG. 2B is a plan view of a cranial prosthetic, which comprises a perforated plate (1), wherein the perforations comprise four holes (2) substantially equidistant from a central point. The plate also comprises an additional hole at the center point (3) indentations suitable for recessing leads (7) with at least one exit point (15), protrusions into the channel (14) and integrated screw holes (13).
Figure 3A:
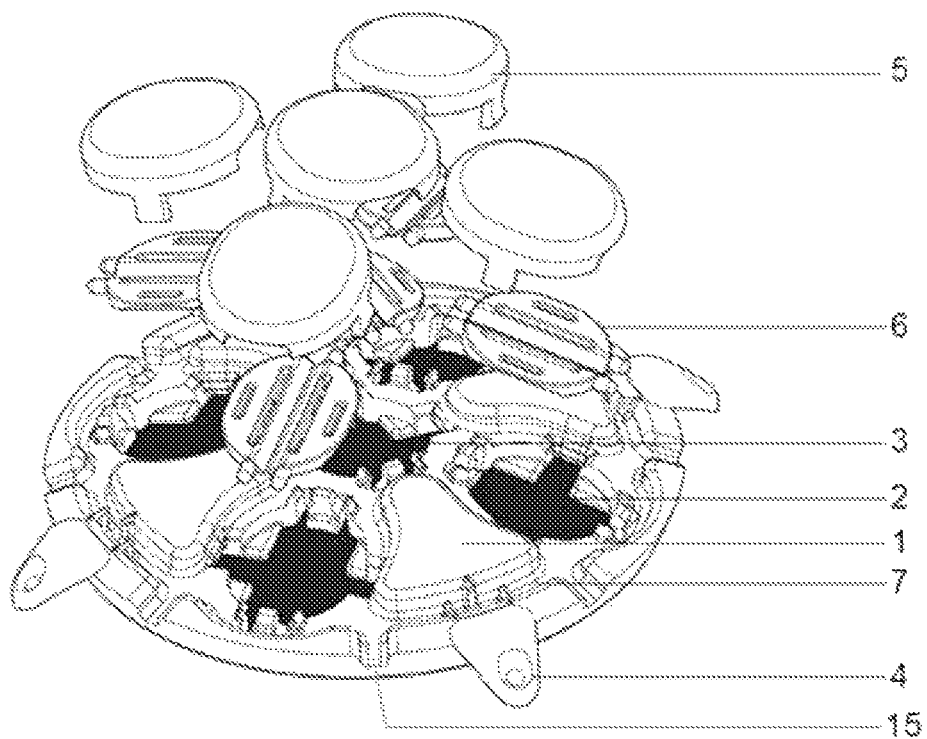
FIG. 3A is a side plan exploded view of a cranial prosthetic, which comprises a curved perforated plate (1), wherein the perforations comprise four holes (2) substantially equidistant from a central point. The plate also comprises an additional hole at the center point (3), detachable screw fixing tabs (4) for attaching the cranial prosthetic to the cranium via screws, detachable securing means consisting of flaps (6) that secure the electrode when closed, and indentations in the form of channels (7) suitable for recessing extension leads with at least one exit point (15), which connect individual electrodes to the main lead. Removable protective caps (5) may be placed over the detachable securing means when closed.
Figure 3B:
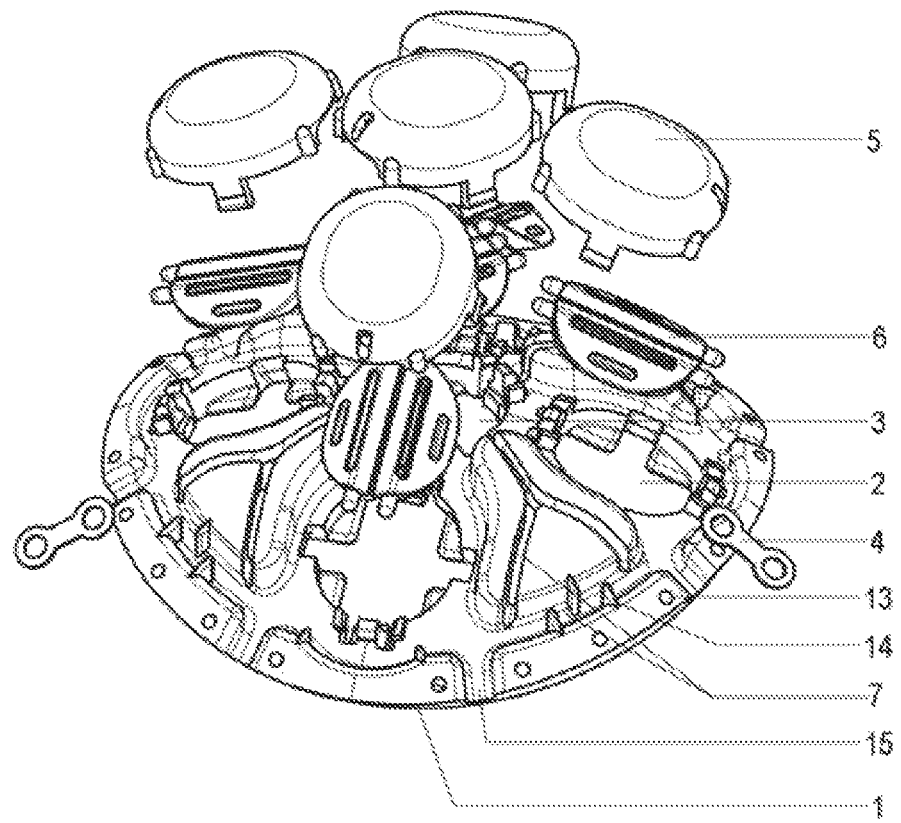
FIG. 3B is a side plan exploded view of a cranial prosthetic, which comprises a curved perforated plate (1), wherein the perforations comprise four holes (2) substantially equidistant from a central point. The plate also comprises an additional hole at the center point (3), detachable screw fixing tabs (4) and screw holes (13) for attaching the cranial prosthetic to the cranium via screws or sutures, detachable securing means consisting of flaps (6) that secure the electrode when closed, and indentations in the form of channels (7) suitable for recessing extension leads with at least one exit point (15), which connect individual electrodes to the main lead and protrusions into the channel (14) that assist with securing the leads in place. Removable protective caps (5) may be placed over the detachable securing means when closed.
Figure 4A:
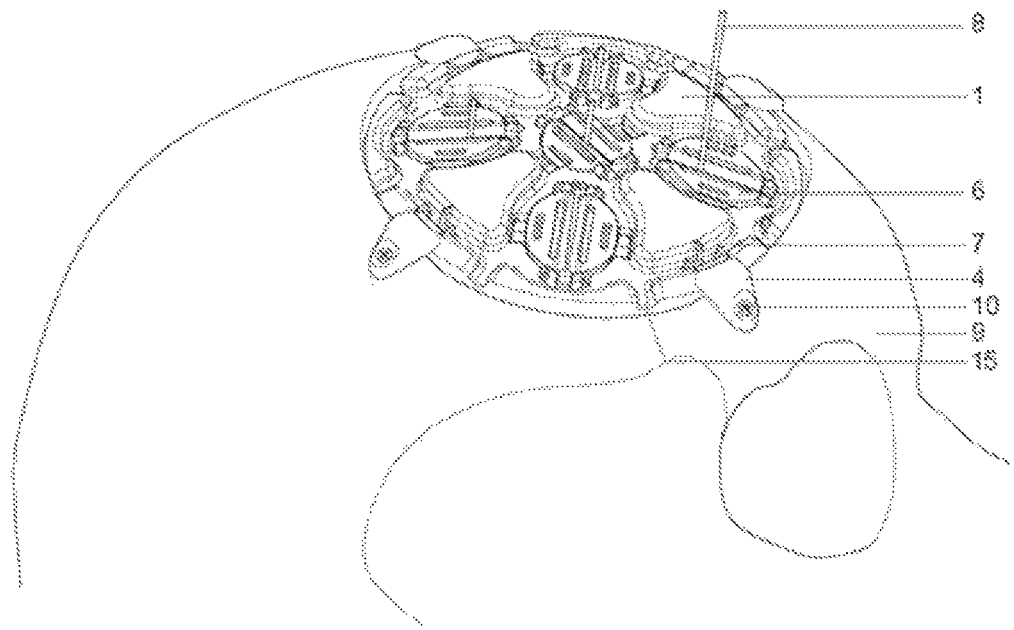
FIG. 4A is an in situ view of a cranial prosthetic, which comprises a curved perforated plate (1), detachable screw fixing tabs (4) for attaching the cranial prosthetic to the cranium (9) via screws (10), detachable securing means consisting of flaps (6) that secure the electrodes (8) when closed, and indentations in the form of channels (7) suitable for recessing extension leads with at least one exit point (15), which connect individual electrodes to the main lead.
Figure 4B:
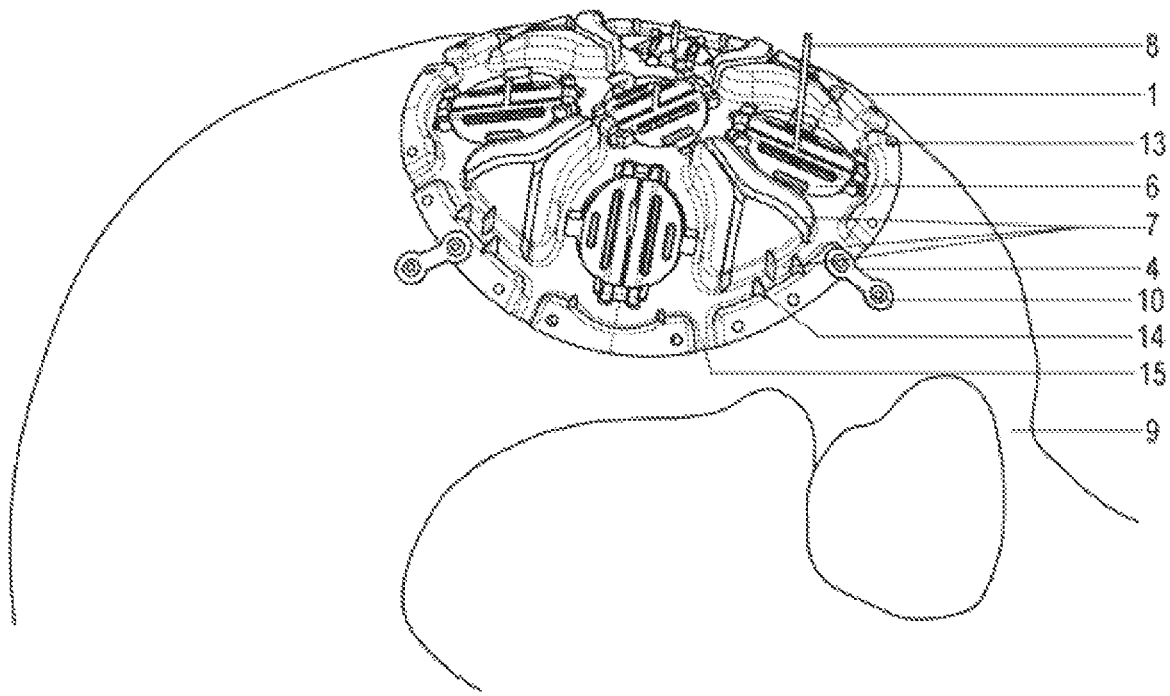
FIG. 4B is an in situ view of a cranial prosthetic, which comprises a curved perforated plate (1), detachable screw fixing tabs (4) and screw holes (13) for attaching the cranial prosthetic to the cranium (9) via screws (10), detachable securing means consisting of flaps (6) that secure the electrodes (8) when closed, and indentations in the form of channels (7) suitable for recessing extension leads with at least one exit point (15), which connect individual electrodes to the main lead and protrusions into the channel (14) that assist with securing the leads in place.
Figure 5A:
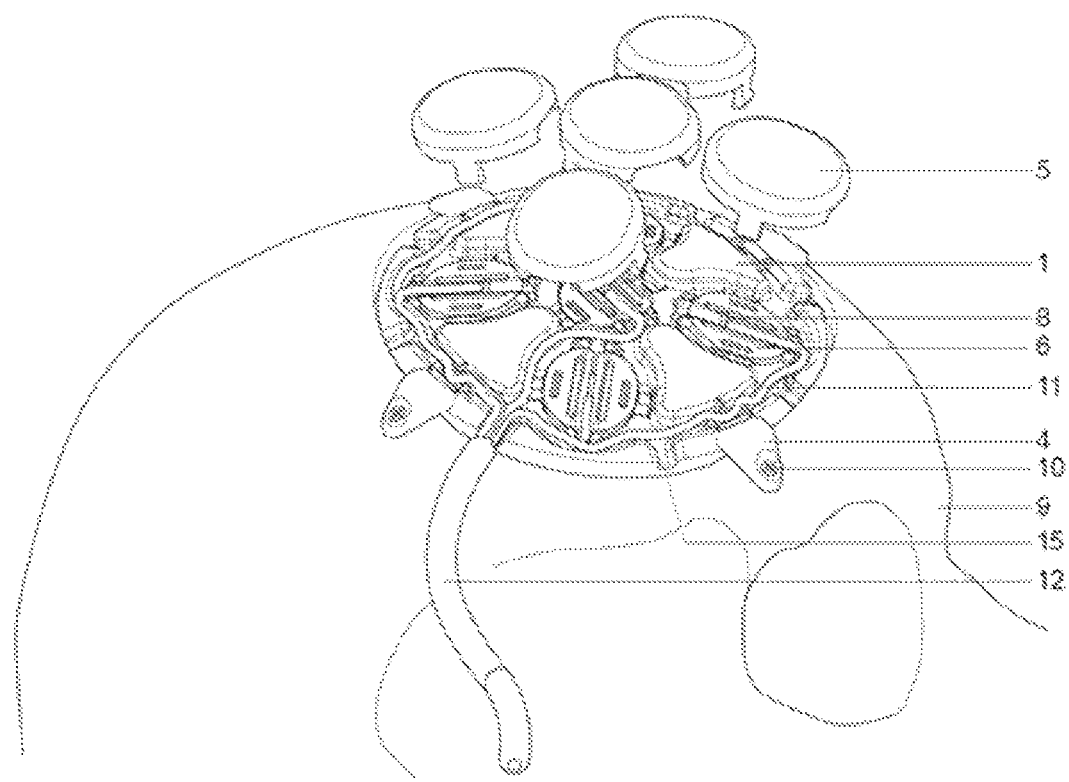
FIG. 5A is an in situ view of a cranial prosthetic, which comprises a curved perforated plate (1), detachable screw fixing tabs (4) for attaching the cranial prosthetic to the cranium (9) via screws (10), detachable securing means consisting of flaps (6) that secure the electrodes (8) when closed. The electrodes are connected to the extension leads (11) which connect individual electrodes to the main lead (12) via one of the exit points (15). Removable protective caps (5) may be placed over the detachable securing means when closed.
Figure 5B:
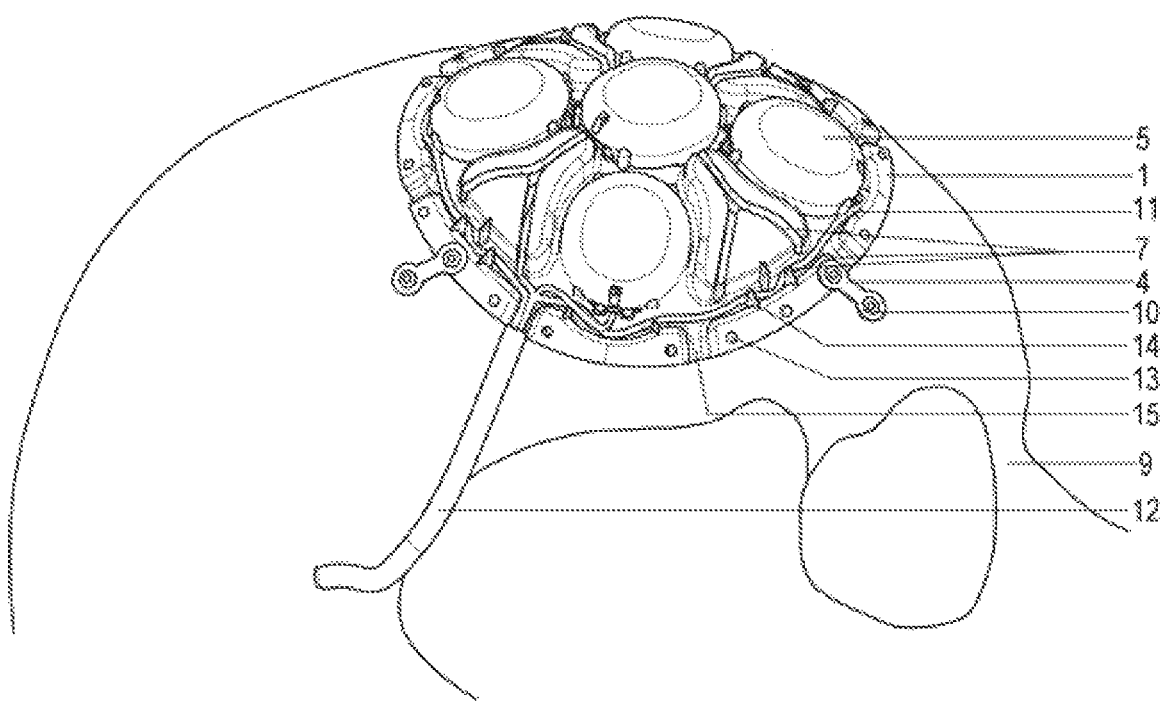
FIG. 5B is an in situ view of a cranial prosthetic, which comprises a curved perforated plate (1), detachable screw fixing tabs (4) and screw holes (13) for attaching the cranial prosthetic to the cranium (9) via screws (10) or sutures. The electrodes are connected to the extension leads (11) placed in indentations in the form of channels (7) and connect individual electrodes to the main lead (12) via one of the exit points (15). Protrusions into the channel (14) assist with securing the leads in place and removable protective caps (5) are placed over the electrodes.
Figure 6:
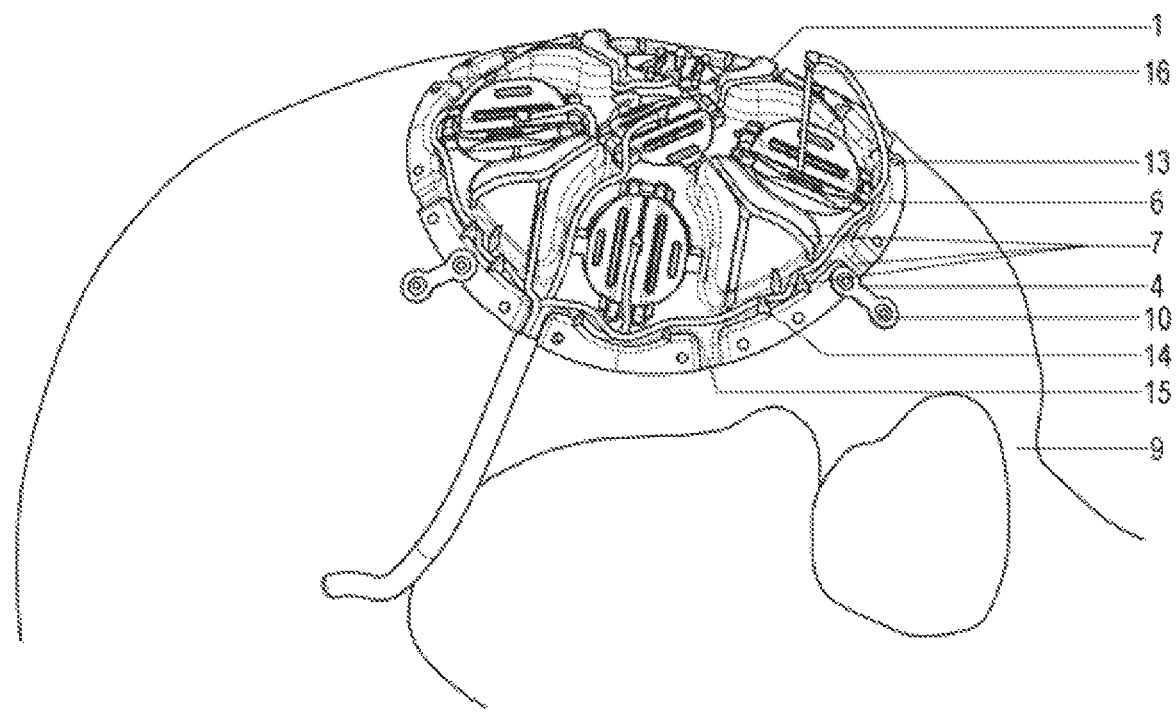
FIG. 6 is an in situ view of a cranial prosthetic with no protective caps, which comprises a curved perforated plate (1), detachable screw fixing tabs (4) and screw holes (13) for attaching the cranial prosthetic to the cranium (9) via screws (10), detachable securing means consisting of flaps (6) that secure the electrodes (16) when closed. The electrodes are connected to the extension leads placed in indentations in the form of channels (7) which connect individual electrodes to the main lead via one of the exit points (15), and protrusions into the channel (14) that assist with securing the leads in place.
Figure 7C:
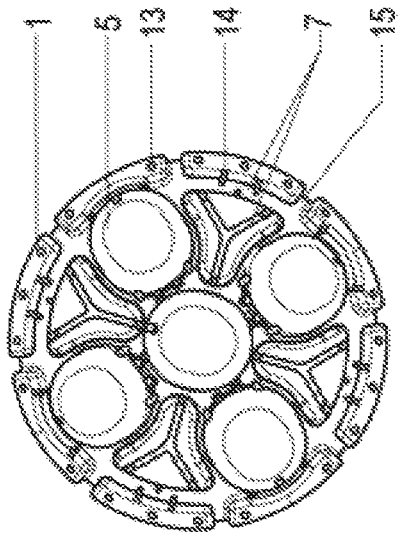
FIGS. 7A, 7B, and 7C are side plan and plan views of the cranial prosthetic, similar to that in FIG. 5B, that illustrates that the cranial prosthetic may comprise a curved perforated plate comprising an asymmetrical curvature, whereby the radius of curvature in one direction is unequal to the radius of curvature in the perpendicular direction, for example an asymmetrical curvature similar to a section of the skull. The cranial prosthetic may be produced in a range of different asymmetric shapes such that a surgeon may select one that most resembles the section of skull removed in surgery. The cranial prosthetic comprises a curved perforated plate (1), removable protective caps (5), indentations in the form of channels (7) suitable for recessing extension leads which connect individual electrodes to the main lead via one of the exit points (15), screw holes (13) for attaching the cranial prosthetic to the cranium, and protrusions into the channel (14) that assist with securing the leads in place.
Figure 7B:
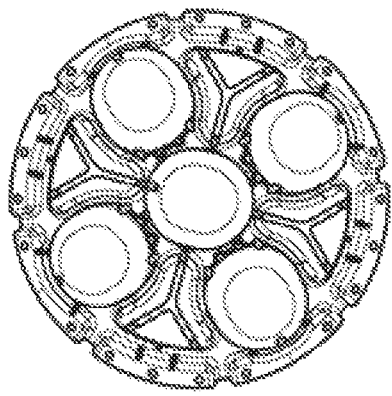
Figure 7A:
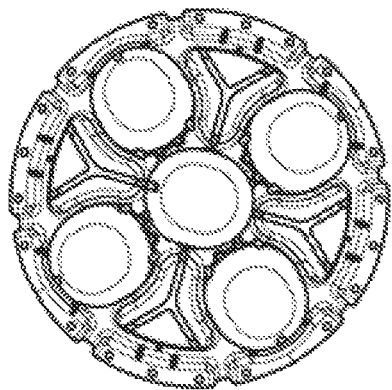

Many embodiments of the invention are detailed throughout the specification and will be apparent to a reader skilled in the art. The invention is not to be interpreted as being limited to any of the recited embodiments.

"A" means "at least one". In any embodiment where "a" is used to denote a given material or element, "a" may mean one.

"Comprising" means that a given material or element may contain other materials or elements. In any embodiment where "comprising" is mentioned the given material or element may be formed of at least 10% w/w, at least 20% w/w, at least 30% w/w, or at least 40% w/w of the material or element. In any embodiment where "comprising" is mentioned, "comprising" may also mean "consisting of" (or "consists of") or "consisting essentially of" (or "consists essentially of") a given material or element.

"Consisting of" or "consists of" means that a given material or element is formed entirely of the material or element. In any embodiment where "consisting of" or "consists of" is mentioned the given material or element may be formed of 100% w/w of the material or element.

"Consisting essentially of" or "consists essentially of" means that a given material or element consists almost entirely of that material or element. In any embodiment where "consisting essentially of" or "consists essentially of" is mentioned the given material or element may be formed of at least 50% w/w, at least 60% w/w, at least 70% w/w, at least 80% w/w, at least 90% w/w, at least 95% w/w or at least 99% w/w of the material or element.

"Substantially" means greater than 50%, at least 60%, at least 70%, at least 80%, at least 90%, at least 95% or at least 99%.

In any embodiment where "comprising" is mentioned, "comprising" may also mean "consisting of" (or "consists of") or "consisting essentially of" (or "consists essentially of") a given material or element.

In any embodiment where "is" or "may be" is used to define a material or element, "is" or "may be" may mean the material or element "consists of" or "consists essentially of" the material or element.

Claims are embodiments.

Embodiments may be combined.

Cranial Prosthetic

Herein, the cranial prosthetic comprises a perforated plate, particularly a perforated plate and indentations suitable for recessing leads, wherein the perforations comprise a plurality of holes substantially equidistant from a central point. The cranial prosthetic typically replaces a portion of the patient's original skull which is removed during surgery. Ideally the cranial prosthetic comprises an outward facing surface designed so as to prevent pressure points on the skin above it.

In one embodiment the cranial prosthetic may comprise one or more materials such as metals (for example titanium and its alloys, stainless steel, and cobalt-chromium-molybdenum alloys), polymers (for example polyether ether ketone, polyethylene, polypropylene, acrylonitrile, butadiene styrene, polysiloxanes, polyamides and polysulfones) and ceramics (for example zirconia, alumina, silicate glass) as well as composites of the aforementioned materials.

In one embodiment the cranial prosthetic may comprise carbon materials such as graphene-based materials.

In one embodiment the cranial prosthetic may comprise a metal cranial prosthetic, for example titanium and its alloys, stainless steel, and cobalt-chromium-molybdenum alloys.

In one embodiment the cranial prosthetic may comprise a polymer cranial prosthetic, for example polyether ether ketone, polyethylene, polypropylene, acrylonitrile, butadiene styrene, polysiloxanes, polyamides and polysulfones.

In one embodiment the cranial prosthetic may comprise a polymer cranial prosthetic.

In one embodiment the cranial prosthetic may comprise polyether ether ketone cranial prosthetic.

In one embodiment the cranial prosthetic may comprise a polyethylene cranial prosthetic.

In one embodiment the cranial prosthetic may comprise a polypropylene cranial prosthetic.

In one embodiment the cranial prosthetic may comprise an acrylonitrile cranial prosthetic.

In one embodiment the cranial prosthetic may comprise a butadiene styrene cranial prosthetic.

In one embodiment the cranial prosthetic may comprise a polysiloxane cranial prosthetic.

In one embodiment the cranial prosthetic may comprise a polyimide cranial prosthetic.

In one embodiment the cranial prosthetic may comprise a polysulfone cranial prosthetic.

In one embodiment the cranial prosthetic may comprise a ceramic, for example zirconia, alumina, and silicate glass cranial prosthetic.

In one embodiment the cranial prosthetic may comprise a curved perforated plate.

In one embodiment the cranial prosthetic may comprise a curved perforated plate, shaped so as to restore the original contour of the skull.

In one embodiment the cranial prosthetic may comprise a curved perforated plate, shaped substantially similar to the removed skull piece.

In one embodiment the cranial prosthetic may comprise a uniform curved perforated plate, wherein the curve is of uniform distribution.

In one embodiment the cranial prosthetic may comprise a non-uniform curved perforated plate wherein the curve is of non-uniform distribution.

In one embodiment the cranial prosthetic may comprise a curved perforated plate comprising an asymmetrical curvature, whereby the radius of curvature in one direction is unequal to the radius of curvature in the perpendicular direction.

In one embodiment the cranial prosthetic may comprise a curved perforated plate comprising an asymmetrical curvature similar to a section of the skull. The cranial prosthetic may be produced in a range of different asymmetric shapes such that a surgeon may select one that most resembles the section of skull removed in surgery.

In one embodiment the cranial prosthetic may be custom manufactured for each patient. Custom manufacture may be achieved, for example, by using their own computer tomography (CT) scans. If the cranial prosthetic is custom manufactured, the replacement piece may more closely replicate their natural cranium and forms a smoother fit with the intact skull.

In one embodiment the cranial prosthetic is substantially circular in shape.

In one embodiment the cranial prosthetic is substantially circular in shape with an average diameter between 1 cm and 15 cm.

In one embodiment the cranial prosthetic is substantially circular in shape with an average diameter between 3 cm and 12 cm.

In one embodiment the cranial prosthetic is circular in shape.

In one embodiment the cranial prosthetic is circular in shape with an average diameter between 1 cm and 15 cm.

In one embodiment the cranial prosthetic is circular in shape with an average diameter between 3 cm and 12 cm.

In one embodiment the cranial prosthetic is circular in shape with an average diameter between 6 cm and 12 cm.

In one embodiment the cranial prosthetic is circular in shape with an average diameter between 8 cm and 10 cm.

In one embodiment the cranial prosthetic has a thickness of <1 cm.

In one embodiment the cranial prosthetic has a thickness of <0.9 cm.

In one embodiment the cranial prosthetic has a thickness of <0.8 cm.

In one embodiment the cranial prosthetic has a thickness of <0.7 cm.

In one embodiment the cranial prosthetic has a thickness of <0.6 cm.

In one embodiment the cranial prosthetic has a thickness of <0.5 cm.

In one embodiment the cranial prosthetic has a thickness of 0.5-0.8 cm.

Indentations Suitable for Recessing Leads

The cranial prosthetic comprises indentations suitable for recessing leads. In one embodiment the cranial prosthetic may comprise a perforated plate, wherein the perforations comprise a plurality of holes substantially equidistant from a central point, and wherein the perforated plate contains additional indentations. These additional indentations may be contained within the body of the plate on the outward facing surface of the plate. In one embodiment the indentations are channels suitable for recessing extension leads which connect individual electrodes to the main lead. In one embodiment wherein the perforated plate contains additional indentations, the additional indentations are channels suitable for recessing extension leads which connect individual electrodes to the main lead. The extension leads may be connected to the electrodes, or they may be part of the electrode itself. The main lead is a lead that may be connected to the charge delivery device. If the extension leads are recessed this makes them less vulnerable to being dislodged once in use.

In one embodiment the indentations suitable for recessing leads comprise a series of interconnecting channels.

In one embodiment the indentations suitable for recessing leads comprise a recessed channel around the perimeter.

In one embodiment the indentations suitable for recessing leads comprise a series of interconnecting channels and a recessed channel around the perimeter.

In one embodiment the indentations suitable for recessing leads comprise a recessed channel around the perimeter of the cranial prosthetic, at least 1 mm from the outer edge.

In one embodiment the indentations suitable for recessing leads comprise a recessed channel around the perimeter of the cranial prosthetic, at least 2 mm from the outer edge.

In one embodiment the indentations suitable for recessing leads comprise a recessed channel around the perimeter of the cranial prosthetic, at least 3 mm from the outer edge.

In one embodiment the indentations suitable for recessing leads comprise a series of interconnecting channels with at least one exit point. The exit point may be a further indentation on the outer perimeter of the cranial prosthetic which allows the extension leads to connect to (or form) the main lead.

In one embodiment the indentations suitable for recessing leads comprise a recessed channel around the perimeter with at least one exit point. In one embodiment at least one exit point is 1-10 exit points. In one embodiment at least one exit point is 4-10 exit points. In one embodiment at least one exit point is 2 exit points. In one embodiment at least one exit point is 4 exit points. In one embodiment at least one exit point is 8 exit points.

In one embodiment the indentations suitable for recessing leads comprise a series of interconnecting channels with a plurality of exit points. A plurality of exit points allows adaptable positioning of the main lead, a decision that can be made during surgery. In one embodiment only one of the exit points would be utilized for connection to the main lead.

In one embodiment the indentations suitable for recessing leads comprise a recessed channel around the perimeter with a plurality of exit points.

In one embodiment the indentations suitable for recessing leads comprise a recessed channel of varying widths around the perimeter. Varying widths allow for narrower sections of the channel that serve to secure the leads in position, acting as pinch points. These varying widths may be accomplished by gradual undulations, or by one or more protrusions into the channel.

Perforations

Herein, the cranial prosthetic comprises a perforated plate and indentations suitable for recessing leads, wherein the perforations comprise a plurality of holes substantially equidistant from a central point.

In one embodiment a plurality of holes refers to at least two holes.

In one embodiment a plurality of holes refers to at least three holes.

In one embodiment a plurality of holes refers to at least four holes.

In one embodiment a plurality of holes refers to at least five holes.

In one embodiment a plurality of holes refers to two holes.

In one embodiment a plurality of holes refers to three holes.

In one embodiment a plurality of holes refers to four holes.

In one embodiment a plurality of holes refers to five holes.

In one embodiment a hole refers to a substantially circular hole.

In one embodiment a hole refers to a circular hole.

In one embodiment a hole refers to a slit.

In one embodiment a hole refers to a cross shaped hole.

In one embodiment there may be more than one plurality of holes substantially equidistant from a central point (e.g., in a concentric circular-type arrangement).

Central Point

Herein, the cranial prosthetic comprises a perforated plate and indentations suitable for recessing leads, wherein the perforations comprise a plurality of holes substantially equidistant from a central point. The central point is relative to the perforations and is not necessarily at the center of the perforated plate, but it can be.

In one embodiment substantially equidistant from a central point means that the closest point of each of the holes is the same distance from the central point ±20%.

In one embodiment substantially equidistant from a central point means that the midpoint of each of the holes is the same distance from the central point ±20%.

In one embodiment substantially equidistant from a central point means that the closest point of each of the holes is the same distance from the central point ±10%.

In one embodiment substantially equidistant from a central point means that the midpoint of each of the holes is the same distance from the central point ±10%.

In one embodiment substantially equidistant from a central point means that the closest point of each of the holes is the same distance from the central point ±5%.

In one embodiment substantially equidistant front a central point means that the midpoint of each of the holes is the same distance from the central point ±5%.

In one embodiment there is an additional hole at the center point. In a further embodiment the hole at the central point is a different shape to the other holes.

Securing Means

In one embodiment the cranial prosthetic additionally comprises securing means for securing an electrode in place within a perforation. This may be particularly useful where the perforations in the plate are bigger than the electrodes. In an open state, the securing means may allow for flexible positioning of the electrodes. In a closed state, the securing means may be used to clamp and secure the position of the electrode. These securing means may be an integral part of the cranial prosthetic, or, alternatively, they may be separate, but attachable to, the cranial prosthetic.

In one embodiment the securing means may comprise a locking component insert, for example one that tightens on locking.

In one embodiment the securing means may comprise ball and socket fixings.

In one embodiment the securing means may comprise threaded locking components.

In one embodiment the securing means may comprise one or more slidable locking components.

In one embodiment the securing means may comprise flaps that secure the electrode when closed. The flaps may be attached to the perforated plate via, a hinge.

In one embodiment the securing means may comprise a clip that pinches the electrodes.

In one embodiment the securing means may comprise a bayonet type fitting.

In one embodiment the securing means may comprise one or more materials such as metals (for example titanium and its alloys, stainless steel, and cobalt-chromium-molybdenum alloys), polymers (for example polyether ether ketone, polyethylene, polypropylene, acrylonitrile, butadiene styrene, polysiloxanes, polyamides and polysulfones) and ceramics (for example zirconia, alumina, silicate glass) as well as composites of the aforementioned materials.

In one embodiment the securing means may comprise carbon materials such as graphene-based materials.

In one embodiment the securing means may comprise a metal, for example titanium and its alloys, stainless steel, and cobalt-chromium-molybdenum alloys.

In one embodiment the securing means may comprise a polymer, for example polyether ether ketone, polyethylene, polypropylene, acrylonitrile, butadiene styrene, polysiloxanes, polyamides and polysulfones.

In one embodiment the securing means may comprise a ceramic, for example zirconia, alumina, and silicate glass.

Protective Cap

In one embodiment protective caps may be placed over the perforations in the plate. These protective caps provide protection for the electrodes and extension leads and assist in holding the electrode in position. The protective caps may be placed directly over the hole or, where additional securing means are employed, these protective caps may be placed over the additional securing means.

In one embodiment the protective cap comprises a low profile protective cap.

In one embodiment the protective cap comprises a push fit protective cap.

In one embodiment the protective cap comprises a plastic protective cap.

In one embodiment the protective cap comprises a polysiloxane protective cap.

In one embodiment the protective cap comprises a polyether ether ketone protective cap.

In one embodiment the protective cap comprises a friction fit protective cap.

In one embodiment the protective cap comprises a snap-fit protective cap.

In one embodiment the protective cap comprises screw fittings.

In one embodiment the protective cap comprises bayonetted fittings.

In one embodiment the protective cap may comprise an electrical contact and integrate the extension leads connecting the implantable electrode to the main lead.

Fixing Means

In one embodiment, the cranial prosthetic may be secured in place within the cranial window.

In one embodiment, glue is used to secure the cranial prosthetic.

In one embodiment the cranial prosthetic includes means for attaching the cranial prosthetic via screws, for example screw fixing tabs. These tabs may be incorporated into the cranial prosthetic or secured onto the cranial prosthetic. Suitable screws include titanium screws.

In one embodiment the cranial prosthetic includes means for attaching the cranial prosthetic via fixing tabs that would enable the placement of suitable screws or the placement of sutures through them.

Alternatively, a series of fixing holes could be introduced along the perimeter edge of the cranial prosthetic. This would enable the fitting of fixing plates, for example titanium bone plates. Alternatively, this would enable the placement of sutures.

Processes

A cranial prosthetic as described may be manufactured via a variety of techniques which comprise injection molding, machining (for example computer numerically controlled machining), casting or 3D printing (for example fused deposition modelling, stereolithography, selective laser sintering).

In one embodiment, there is provided a process for the manufacture of a cranial prosthetic as described herein which comprises injection molding.

In one embodiment, there is provided a process for the manufacture of a cranial prosthetic as described herein which comprises machining (for example computer numerically controlled machining).

In one embodiment, there is provided a process for the manufacture of a cranial prosthetic as described herein which comprises casting.

In one embodiment, there is provided a process for the manufacture of a cranial prosthetic as described herein which comprises 3D printing (for example fused deposition modelling, stereolithography, selective laser sintering).

Using the Cranial Prosthetic

The cranial prosthetic as described herein may be employed in a method of electrotherapy during an operation comprising the following procedure:
1. Make a scalp incision & fold back the skin flap;
2. Open a cranial window large enough to accommodate the prosthetic and discard the bone;
3. Fit prosthetic to cover cranial window and fix in place;
4. Insert electrodes;
5. Secure electrodes in place;
6. Cut electrodes to length;
7. Fit extension lead to electrodes;
8. Optionally fit protective cap over electrodes to secure;
9. Organize wiring into channels ensuring a low profile, secure in place;
10. Replace skin flap and suture closed;
11. Connect main lead to charge delivery device.

Alternatively, the cranial prosthetic as described herein may be employed in a method of electrotherapy during an operation comprising the following procedure:
1. Make a scalp incision retract the skin flap;
2. Open a cranial window large enough to accommodate the prosthetic and discard the bone;
3. Fit prosthetic to cover cranial window and fix in place;
4. Insert electrodes;
5. Secure electrodes in place;
6. Optionally cut electrodes to length;
7. Optionally fit extension lead to electrodes if not already integrated with the electrodes or the protective cap;
8. Optionally fit protective cap over electrodes to secure or make electrical contact;
9. Organize wiring into channels ensuring a low profile, secure in place;
10. Replace skin flap and suture closed;
11. Connect main lead to charge delivery device.

Electrotherapy

In one embodiment there is provided electrotherapy comprising a cranial prosthetic which comprises a perforated plate and indentations suitable for recessing leads, wherein the perforations comprise a plurality of holes substantially equidistant from a central point.

In one embodiment there is provided multi-electrode electrotherapy comprising a cranial prosthetic, which comprises a perforated plate and indentations suitable for recessing leads, wherein the perforations comprise a plurality of holes substantially equidistant from a central point.

In one embodiment there is provided electrotherapy comprising a cranial prosthetic as described herein. In one embodiment electrotherapy refers to multi-electrode electrotherapy. Electrotherapy is the use of electrical energy as a medical treatment.

In one embodiment there is provided the use of electrotherapy comprising a cranial prosthetic as described herein for the treatment of:
- brain tumors (including Grade I, II, III or IV glioma; pilocytic astrocytoma; subependymal giant cell astrocytoma; diffuse astrocytoma; oligodendroglioma; oligodendroglioma NOS; anaplastic astrocytoma; anaplastic oligodendroglioma; anaplastic oligodendroglioma NOS; glioblastoma; giant-cell glioblastoma; glioblastoma multiforme; subependymal giant cell astrocytoma; pilomyxoid astrocytoma; pleomorphic xanthoastrocytoma; ganglioglioma; oligoastrocytoma; meningiomas (including grade I, II or III meningioma and other neoplasms related to the meninges (for example haemangiopericytoma)); pediatric brain tumors (including ependymoma, medulloblastoma, atypical teratoid/rhabdoid tumor (AT/RT); choroid plexus papilloma; choroid plexus carcinoma; intracranial teratoma; and embryonal tumors with multilayered rosettes (ETMR)), pineal region tumors (for example pineoblastoma), and pituitary region tumors (for example pituitary adenoma craniopharyngioma, and chordoma);
- brain metastasis (for example brain metastases from lung cancer, breast cancer, genitourinary tract cancer, osteosarcoma and melanoma);
- stimulation of the nervous tissue for the treatment of or symptom relief from neurological conditions (for example enhancing neurological recovery after brain damage from stroke/traumatic injury);
- recording of the activity of the brain for diagnostic purposes or to enable brain—computer interface communications;
- deep brain stimulation (for example treatment of movement disorders (for example Parkinson's disease, essential tremor, and dystonia) and psychiatric symptoms (for example anxiety, insomnia, depression, hypervigilance, and obsessive compulsive disease);
- pain management; or
- wound healing.

In one embodiment there is provided the use of electrotherapy comprising a cranial prosthetic as described herein for the treatment of diffuse midline glioma.

In one embodiment there is provided the use of electrotherapy comprising a cranial prosthetic as described herein for the stimulation of seizure onset zones for the treatment of or symptom relief from drug-resistant epilepsy.

In one embodiment there is provided the use of electrotherapy comprising a cranial prosthetic as described herein for adjuvant therapy.

In one embodiment there is provided the use of electrotherapy comprising a cranial prosthetic as described herein for the treatment of brain tumors.

In one embodiment there is provided the use of electrotherapy comprising a cranial prosthetic as described herein for the treatment of a Grade I, II, III or IV glioma.

In one embodiment there is provided the use of electrotherapy comprising a cranial prosthetic as described herein for the treatment of a Grade I glioma.

In one embodiment there is provided the use of electrotherapy comprising a cranial prosthetic as described herein for the treatment of pilocytic astrocytoma.

In one embodiment there is provided the use of electrotherapy comprising a cranial prosthetic as described herein for the treatment of a Grade II glioma.

In one embodiment there is provided the use of electrotherapy comprising a cranial prosthetic as described herein for the treatment of diffuse astrocytoma or oligodendroglioma.

In one embodiment there is provided the use of electrotherapy comprising a cranial prosthetic as described herein for the treatment of a Grade III glioma.

In one embodiment there is provided the use of electrotherapy comprising a cranial prosthetic as described herein for the treatment of anaplastic astrocytoma or anaplastic oligodendroglioma.

In one embodiment there is provided the use of electrotherapy comprising a cranial prosthetic as described herein for the treatment of a Grade IV glioma.

In one embodiment there is provided the use of electrotherapy comprising a cranial prosthetic as described herein for the treatment of giant-cell glioblastoma or glioblastoma multiforme.

In one embodiment there is provided the use of electrotherapy comprising a cranial prosthetic as described herein for the treatment of glioblastoma multiforme.

In one embodiment there is provided the use of electrotherapy comprising a cranial prosthetic as described herein for the treatment of brain tumors following surgical resection.

In one embodiment there is provided the use of electrotherapy comprising a cranial prosthetic as described herein for the treatment of a Grade I, II, III or IV glioma following surgical resection.

In one embodiment there is provided the use of electrotherapy comprising a cranial prosthetic as described herein for the treatment of a Grade I glioma following surgical resection.

In one embodiment there is provided the use of electrotherapy comprising a cranial prosthetic as described herein for the treatment of pilocytic astrocytoma following surgical resection.

In one embodiment there is provided the use of electrotherapy comprising a cranial prosthetic as described herein for the treatment of a Grade II glioma following surgical resection.

In one embodiment there is provided the use of electrotherapy comprising a cranial prosthetic as described herein for the treatment of diffuse astrocytoma or oligodendroglioma following surgical resection.

In one embodiment there is provided the use of electrotherapy comprising a cranial prosthetic as described herein for the treatment of a Grade III glioma following surgical resection.

In one embodiment there is provided the use of electrotherapy comprising a cranial prosthetic as described herein for the treatment of anaplastic astrocytoma or anaplastic oligodendroglioma following surgical resection.

In one embodiment there is provided the use of electrotherapy comprising a cranial prosthetic as described herein for the treatment of a Grade IV glioma following surgical resection.

In one embodiment there is provided the use of electrotherapy comprising a cranial prosthetic as described herein for the treatment of diffuse midline glioma.

In one embodiment there is provided the use of electrotherapy comprising a cranial prosthetic as described herein for the treatment of brain metastases.

In one embodiment there is provided the use of electrotherapy comprising a cranial prosthetic as described herein for the treatment of or symptom relief from drug-resistant epilepsy.

In one embodiment there is provided the use of electrotherapy comprising a cranial prosthetic as described herein for the treatment of giant-cell glioblastoma or glioblastoma multiforme following surgical resection.

In one embodiment there is provided the use of electrotherapy comprising a cranial prosthetic as described herein for the treatment of glioblastoma multiforme following surgical resection.

Use

In one embodiment there is provided a cranial prosthetic for use in electrotherapy, which comprises a perforated plate, wherein the perforations comprise a plurality of holes substantially equidistant from a central point.

In one embodiment there is provided a cranial prosthetic for use in multi-electrode electrotherapy, which comprises a perforated plate, wherein the perforations comprise a plurality of holes substantially equidistant from a central point.

In one embodiment there is provided a cranial prosthetic for use in electrotherapy, which comprises a perforated plate and indentations suitable for recessing leads, wherein the perforations comprise a plurality of holes substantially equidistant from a central point.

In one embodiment there is provided a cranial prosthetic for use in multi-electrode electrotherapy, which comprises a perforated plate and indentations suitable for recessing leads, wherein the perforations comprise a plurality of holes substantially equidistant from a central point.

In one embodiment there is provided a cranial prosthetic as described herein for use in electrotherapy. In one embodiment electrotherapy refers to multi-electrode electrotherapy. Electrotherapy is the use of electrical energy as a medical treatment.

In one embodiment there is provided a cranial prosthetic as described herein for use in the electrotherapy treatment of:
  brain tumors (including Grade I, II, III or IV glioma; pilocytic astrocytoma; subependymal giant cell astrocytoma; diffuse astrocytoma; oligodendroglioma; oligodendroglioma NOS; anaplastic astrocytoma; anaplastic oligodendroglioma; anaplastic oligodendroglioma NOS; glioblastoma; giant-cell glioblastoma; glioblastoma multiforme; subependymal giant cell astrocytoma; pilomyxoid astrocytoma; pleomorphic xanthoastrocytoma; ganglioglioma; oligoastrocytoma; meningiomas (including grade I, II or III meningioma and other neoplasms related to the meninges (for example haemangiopericytoma)); pediatric brain tumors (including ependymoma, medulloblastoma, atypical teratoid/rhabdoid tumor (AT/RT); choroid plexus papilloma, choroid plexus carcinoma; intracranial teratoma; and embryonal tumors with multilayered rosettes (ETMR)), pineal region tumors (for example pineoblastoma), and pituitary region tumors (for example pituitary adenoma, craniopharyngioma, and chordoma);
  brain metastasis (for example brain metastases from lung cancer, breast cancer, genitourinary tract cancer, osteosarcoma, and melanoma);
  stimulation of the nervous tissue for the treatment of or symptom relief from neurological conditions (for example enhancing neurological recovery after brain damage from stroke/traumatic injury); recording of the activity of the brain for diagnostic purposes or to enable brain—computer interface communications;
  deep brain stimulation (for example treatment of movement disorders (for example Parkinson's disease, essential tremor, and dystonia) and psychiatric symptoms (for example anxiety, insomnia, depression, hypervigilance, and obsessive compulsive disease);
  pain management; or
  wound healing.

In one embodiment there is provided a cranial prosthetic as described herein for use in the electrotherapy treatment of diffuse midline glioma.

In one embodiment there is provided a cranial prosthetic as described herein for use in the electrotherapy treatment of or symptom relief from drug-resistant epilepsy.

In one embodiment there is provided a cranial prosthetic as described herein for use in adjuvant therapy.

In one embodiment there is provided a cranial prosthetic as described herein for use in the electrotherapy treatment of brain tumors.

In one embodiment there is provided a cranial prosthetic as described herein for use in the electrotherapy treatment of a Grade I, II, III or IV glioma.

In one embodiment there is provided a cranial prosthetic as described herein for use in the electrotherapy treatment of a Grade I glioma.

In one embodiment there is provided a cranial prosthetic as described herein for use in the electrotherapy treatment of pilocytic astrocytoma.

In one embodiment there is provided a cranial prosthetic as described herein for use in the electrotherapy treatment of a Grade II glioma.

In one embodiment there is provided a cranial prosthetic as described herein for use in the electrotherapy treatment of diffuse astrocytoma or oligodendroglioma.

In one embodiment there is provided a cranial prosthetic as described herein for use in the electrotherapy treatment of a Grade III glioma.

In one embodiment there is provided a cranial prosthetic as described herein for use in the electrotherapy treatment of anaplastic astrocytoma or anaplastic oligodendroglioma.

In one embodiment there is provided a cranial prosthetic as described herein for use in the electrotherapy treatment of a Grade IV glioma.

In one embodiment there is provided a cranial prosthetic as described herein for use in the electrotherapy treatment of diffuse midline glioma.

In one embodiment there is provided a cranial prosthetic as described herein for use in the electrotherapy treatment of brain metastases.

In one embodiment there is provided a cranial prosthetic as described herein for use in the electrotherapy treatment of or symptom relief from drug-resistant epilepsy.

In one embodiment there is provided a cranial prosthetic as described herein for use in the electrotherapy treatment of giant-cell glioblastoma or glioblastoma multiforme.

In one embodiment there is provided a cranial prosthetic as described herein for use in the electrotherapy treatment of glioblastoma multiforme.

In one embodiment there is provided a cranial prosthetic as described herein for use in the electrotherapy treatment of brain tumors following surgical resection.

In one embodiment there is provided a cranial prosthetic as described herein for use in the electrotherapy treatment of a Grade I. II, III or IV glioma following surgical resection.

In one embodiment there is provided a cranial prosthetic as described herein for use in the electrotherapy treatment of a Grade I glioma following surgical resection.

In one embodiment there is provided a cranial prosthetic as described herein for use in the electrotherapy treatment of pilocytic astrocytoma following surgical resection.

In one embodiment there is provided a cranial prosthetic as described herein for use in the electrotherapy treatment of a Grade II glioma following surgical resection.

In one embodiment there is provided a cranial prosthetic as described herein for use in the electrotherapy treatment of diffuse astrocytoma or oligodendroglioma following surgical resection.

In one embodiment there is provided a cranial prosthetic as described herein for use in the electrotherapy treatment of a Grade III glioma following surgical resection.

In one embodiment there is provided a cranial prosthetic as described herein for use in the electrotherapy treatment of anaplastic astrocytoma or anaplastic oligodendroglioma following surgical resection.

In one embodiment there is provided a cranial prosthetic as described herein for use in the electrotherapy treatment of a Grade IV glioma following surgical resection.

In one embodiment there is provided a cranial prosthetic as described herein for use in the electrotherapy treatment of giant-cell glioblastoma or glioblastoma multiforme following surgical resection.

In one embodiment there is provided a cranial prosthetic as described herein for use in the electrotherapy treatment of glioblastoma multiforme following surgical resection.

Methods of Treatment

According to a further embodiment there is provided a cranial prosthetic, as defined herein for use in a method of treatment of the human or animal body by therapy.

According to a further embodiment there is provided a cranial prosthetic, as defined herein for use in a method of electrotherapy of the human or animal body by therapy.

According to a further feature of this embodiment there is provided a method of electrotherapy in a warm-blooded animal, such as man, which comprises administering electrotherapy to said animal comprising a cranial prosthetic as defined herein.

According to a further feature of this embodiment there is provided a method of treating:
- brain tumors (including Grade I, II, III or IV glioma; pilocytic astrocytoma; subependymal giant cell astrocytoma; diffuse astrocytoma; oligodendroglioma; oligodendroglioma NOS; anaplastic astrocytoma; anaplastic oligodendroglioma; anaplastic oligodendroglioma NOS; glioblastoma; giant-cell glioblastoma; glioblastoma multiforme; subependymal giant cell astrocytoma; pilomyxoid astrocytoma; pleomorphic xanthoastrocytoma; ganglioglioma; oligoastrocytoma; meningiomas (including grade I, II or III meningioma and other neoplasms related to the meninges (for example haemangiopericytoma)); pediatric brain tumors (including ependymoma, medulloblastoma, atypical teratoid/rhabdoid tumor (AT/RT); choroid plexus papilloma; choroid plexus carcinoma; intracranial teratoma; and embryonal tumors with multilayered rosettes (ETMR)), pineal region tumors (for example pineoblastoma), and pituitary region tumors (for example pituitary adenoma, craniopharyngioma, and chordoma);
- brain metastasis (for example brain metastases from lung cancer, breast cancer, genitourinary tract cancer, osteosarcoma, and melanoma);
- stimulation of the nervous tissue for the treatment of or symptom relief from neurological conditions (for example enhancing neurological recovery after brain damage from stroke/traumatic injury);
- recording of the activity of the brain for diagnostic purposes or to enable brain—computer interface communications;
- deep brain stimulation (for example treatment of movement disorders (for example Parkinson's disease, essential tremor, and dystonia) and psychiatric symptoms (for example anxiety, insomnia, depression, hypervigilance, and obsessive compulsive disease);
- pain management; or
- wound healing in a warm-blooded animal, such as man, which comprises administering electrotherapy to said animal comprising a cranial prosthetic as defined herein.

According to a further feature of this embodiment there is provided a method of treating diffuse midline glioma in a warm-blooded animal, such as man, which comprises administering electrotherapy to said animal comprising a cranial prosthetic as defined herein.

According to a further feature of this embodiment there is provided a method of treating of or providing symptom relief from drug-resistant epilepsy in a warm-blooded animal, such as man, which comprises administering electrotherapy to said animal comprising a cranial prosthetic as defined herein.

According to a further feature of this embodiment there is provided a method of treating brain tumors in a warm-blooded animal, such as man, which comprises administering electrotherapy to said animal comprising a cranial prosthetic as defined herein.

According to a further feature of this embodiment there is provided a method of treating a Grade I, II, III or IV glioma in a warm-blooded animal, such as man, which comprises administering electrotherapy to said animal comprising a cranial prosthetic as defined herein.

According to a further feature of this embodiment there is provided a method of treating a Grade I glioma in a warm-blooded animal, such as man, which comprises administering electrotherapy to said animal comprising a cranial prosthetic as defined herein.

According to a further feature of this embodiment there is provided a method of treating pilocytic astrocytoma in a warm-blooded animal, such as man, which comprises administering electrotherapy to said animal comprising a cranial prosthetic as defined herein.

According to a further feature of this embodiment there is provided a method of treating a Grade II glioma in a warm-blooded animal, such as man, which comprises administering electrotherapy to said animal comprising a cranial prosthetic as defined herein.

According to a further feature of this embodiment there is provided a method of treating astrocytoma or oligodendroglioma in a warm-blooded animal, such as man, which comprises administering electrotherapy to said animal comprising a cranial prosthetic as defined herein.

According to a further feature of this embodiment there is provided a method of treating a Grade III glioma in a warm-blooded animal, such as man, which comprises administering electrotherapy to said animal comprising a cranial prosthetic as defined herein.

According to a further feature of this embodiment there is provided a method of treating anaplastic astrocytotna or anaplastic oligodendroglioma in a warm-blooded animal, such as man, which comprises administering electrotherapy to said animal comprising a cranial prosthetic as defined herein.

According to a further feature of this embodiment there is provided a method of treating a Grade IV glioma in a warm-blooded animal, such as man, which comprises administering electrotherapy to said animal comprising a cranial prosthetic as defined herein.

According to a further feature of this embodiment there is provided a method of treating diffuse midline glioma in a warm-blooded animal, such as man, which comprises administering electrotherapy to said animal comprising a cranial prosthetic as defined herein.

According to a further feature of this embodiment there is provided a method of treating brain metastases in a warm-blooded animal, such as man, which comprises administering electrotherapy to said animal comprising a cranial prosthetic as defined herein.

According to a further feature of this embodiment there is provided a method of treating or providing symptom relief from drug-resistant epilepsy in a warm-blooded animal, such as man, which comprises administering electrotherapy to said animal comprising a cranial prosthetic as defined herein.

According to a further feature of this embodiment there is provided a method of treating giant-cell glioblastoma or glioblastoma multiforme in a warm-blooded animal, such as man, which comprises administering electrotherapy to said animal comprising a cranial prosthetic as defined herein.

According to a further feature of this embodiment there is provided a method of treating glioblastoma multiforme in a warm-blooded animal, such as man, which comprises administering electrotherapy to said animal comprising a cranial prosthetic as defined herein.

According to a further feature of this embodiment there is provided a method of treating brain tumors following surgical resection in a warm-blooded animal, such as man, which comprises administering electrotherapy to said animal comprising a cranial prosthetic as defined herein.

According to a further feature of this embodiment there is provided a method of treating a Grade I, II, III or IV glioma following surgical resection in a warm-blooded animal, such as man, which comprises administering electrotherapy to said animal comprising a cranial prosthetic as defined herein.

According to a further feature of this embodiment there is provided a method of treating a Grade I glioma following surgical resection in a warm-blooded animal, such as man, which comprises administering electrotherapy to said animal comprising a cranial prosthetic as defined herein.

According to a further feature of this embodiment there is provided a method of treating pilocytic astrocytoma following surgical resection in a warm-blooded animal, such as man, which comprises administering electrotherapy to said animal comprising a cranial prosthetic as defined herein.

According to a further feature of this embodiment there is provided a method of treating a Grade II glioma following surgical resection in a warm-blooded animal, such as man, which comprises administering electrotherapy to said animal comprising a cranial prosthetic as defined herein.

According to a further feature of this embodiment there is provided a method of treating diffuse astrocytoma or oligodendroglioma following surgical resection in a warm-blooded animal, such as man, which comprises administering electrotherapy to said animal comprising a cranial prosthetic as defined herein.

According to a further feature of this embodiment there is provided a method of treating a Grade III glioma following surgical resection in a warm-blooded animal, such as man, which comprises administering electrotherapy to said animal comprising a cranial prosthetic as defined herein.

According to a further feature of this embodiment there is provided a method of treating anaplastic astrocytoma or anaplastic oligodendroglioma following surgical resection in a warm-blooded animal, such as man, which comprises administering electrotherapy to said animal comprising a cranial prosthetic as defined herein.

According to a further feature of this embodiment there is provided a method of treating a Grade IV glioma following surgical resection in a warm-blooded animal, such as man, which comprises administering electrotherapy to said animal comprising a cranial prosthetic as defined herein.

According to a further feature of this embodiment there is provided a method of treating diffuse midline glioma following surgical resection in a warm-blooded animal, such as man, which comprises administering electrotherapy to said animal comprising a cranial prosthetic as defined herein.

According to a further feature of this embodiment there is provided a method of treating brain metastases following surgical resection in a warm-blooded animal, such as man, which comprises administering electrotherapy to said animal comprising a cranial prosthetic as defined herein.

According to a further feature of this embodiment there is provided a method of treating or providing symptom relief from drug-resistant epilepsy in a warm-blooded animal, such as man, which comprises administering electrotherapy to said animal comprising a cranial prosthetic as defined herein.

According to a further feature of this embodiment there is provided a method of treating giant-cell glioblastoma or glioblastoma multiforme following surgical resection in a warm-blooded animal, such as man, which comprises administering electrotherapy to said animal comprising a cranial prosthetic as defined herein.

According to a further feature of this embodiment there is provided a method of treating glioblastoma multiforme following surgical resection in a warm-blooded animal, such as man, which comprises administering electrotherapy to said animal comprising a cranial prosthetic as defined herein.

Kits

In one embodiment there is provided a kit comprising:
a) a cranial prosthetic as described herein;
b) one or more electrodes;
c) a charge delivery device.

In one embodiment there is provided a kit comprising:
a) a cranial prosthetic as described herein; and
b) one or more electrodes.

In one embodiment there is provided a kit comprising:
a) a cranial prosthetic as described herein; and
b) a charge delivery device.

To better illustrate the systems and methods disclosed herein, a non-limiting list of examples of the subject matter disclosed herein (referred to as "STATEMENTS") are provided here:

Statement 1: A cranial prosthetic, which comprises a perforated plate, wherein the perforations comprise a plurality of holes substantially equidistant from a central point.

Statement 2: A cranial prosthetic as stated in Statement 1, wherein the perforations comprise a plurality of at least four holes substantially equidistant from the central point.

Statement 3: A cranial prosthetic as stated in either Statement 1 or Statement 2, which comprises an additional hole at the central point.

Statement 4: A cranial prosthetic as stated in any one of Statements 1-3, which comprises a curved perforated plate.

Statement 5: A cranial prosthetic as stated in any one of Statements 1-4, which comprises indentations suitable for recessing leads.

Statement 6: A cranial prosthetic as stated in any one of Statements 1-5, which is substantially circular in shape.

Statement 7: A cranial prosthetic as stated in any one of Statements 1-6, which comprises securing means for securing an electrode in place within a perforation.

Statement 8: A cranial prosthetic as stated in any one of Statements 1-7, which comprises protective caps placed over the perforations to assist in holding the electrode in position.

Statement 9: A cranial prosthetic as stated in any one of Statements 1-8, which comprises means for attaching the cranial prosthetic to the cranium via screws.

Statement 10: A cranial prosthetic as stated any one of Statements 1-9, which is a metal, polymer and/or ceramic cranial prosthetic.

Statement 11: A process for the manufacture of a cranial prosthetic as stated in any one of Statements 1-10, which comprises injection molding, machining, casting or 3D printing the cranial prosthetic.

Statement 12: A cranial prosthetic as stated in any one of Statements 1-10 for use in electrotherapy.

Statement 13: A cranial prosthetic as stated in any one of Statements 1-10 for use in the electrotherapy treatment of:
- brain tumors (including Grade I, II, III or IV glioma; pilocytic astrocytoma; subependymal giant cell astrocytoma; diffuse astrocytoma, oligodendroglioma; oligodendroglioma NOS; anaplastic astrocytoma; anaplastic oligodendroglioma; anaplastic oligodendroglioma NOS; glioblastoma; giant-cell glioblastoma; glioblastoma multiforme; subependymal giant cell astrocytoma; pilomyxoid astrocytoma, pleomorphic xanthoastrocytoma; ganglioglioma; oligoastrocytoma; meningiomas (including grade I, II or III meningioma and other neoplasms related to the meninges (for example haemangiopericytoma)); pediatric brain tumors (including ependymoma, medulloblastoma, atypical teratoid/rhabdoid tumor (AT/RT); choroid plexus papilloma; choroid plexus carcinoma; intracranial teratoma; and embryonal tumors with multilayered rosettes (ETMR)), pineal region tumors (for example pineoblastoma), and pituitary region tumors (for example pituitary adenoma, craniopharyngioma, and chordoma);
- brain metastasis (for example brain metastases from lung cancer, breast cancer, genitourinary tract cancer, osteosarcoma and melanoma);
- stimulation of the nervous tissue for the treatment of or symptom relief from neurological conditions (for example enhancing neurological recovery after brain damage from stroke/traumatic injury);
- recording of the activity of the brain for diagnostic purposes or to enable brain—computer interface communications;
- deep brain stimulation (for example treatment of movement disorders (for example Parkinson's disease, essential tremor, and dystonia) and psychiatric symptoms (for example anxiety, insomnia, depression, hypervigilance, and obsessive compulsive disease);
- pain management; or
- wound healing.

Statement 14: A cranial prosthetic as stated in any one of Statements 1-10 for use in the electrotherapy treatment of brain tumors.

Statement 15: A method of treating glioblastoma multiforme in a warm-blooded animal, such as man, which comprises administering electrotherapy to said animal comprising a cranial prosthetic as stated in any one of Statements 1-10.

Statement 16. A kit comprising:
a) a cranial prosthetic as stated in any one of Statements 1-10;
b) one or more electrodes;
c) a charge delivery device.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A cranial prosthetic comprising a perforated plate including perforations and indentations suitable for recessing and organizing leads, wherein the perforations comprise a plurality of holes through the perforated plate that are substantially equidistant from a central point of the perforated plate.

2. A cranial prosthetic as recited in claim 1, wherein the perforations comprise four holes through the perforated plate that are substantially equidistant from the central point.

3. A cranial prosthetic as recited in claim 1, further comprising an additional hole through the perforated plate at the central point.

4. A cranial prosthetic as recited in claim 1, wherein the perforated plate is a curved perforated plate.

5. A cranial prosthetic as recited in claim 1, wherein the indentations suitable for recessing and organizing leads comprise a series of interconnecting channels and a recessed channel around a perimeter of the perforated plate.

6. A cranial prosthetic as recited in claim 1, wherein the indentations suitable for recessing and organizing leads comprise a recessed channel around a perimeter of the perforated plate with a plurality of exit points.

7. A cranial prosthetic as recited in claim 1, wherein the perforated plate is substantially circular in shape.

8. A cranial prosthetic as recited in claim 1, further comprising securing means for securing an electrode in place within a perforation.

9. A cranial prosthetic as recited in claim 1, further comprising a protective cap placed over each of the perforations to assist in holding an electrode in position.

10. A cranial prosthetic as recited in claim 1, further comprising means for attaching the perforated plate to a cranium of a patient via screws or sutures.

11. A cranial prosthetic as recited claim 1, wherein the perforated plate is formed from at least one of: a metal, a polymer, and a ceramic.

12. A process for the manufacture of a cranial prosthetic as recited in claim 1, wherein the perforated plate is formed by injection molding, machining, casting, or 3D printing.

13. A method of electrotherapy comprising using a cranial prosthetic as recited in claim 1.

14. A method of treating brain tumors in a human, which comprises administering electrotherapy to the human using a cranial prosthetic as recited in claim 1.

15. A method of treating glioblastoma multiforme in a human, which comprises administering electrotherapy to the human using a cranial prosthetic as recited in claim 1.

16. A kit comprising:
a) a cranial prosthetic as recited in claim 1;
b) one or more electrodes; and
c) a charge delivery device.

17. A cranial prosthetic as recited in claim 1, wherein the indentations suitable for recessing and organizing leads comprise a series of interconnecting channels.

* * * * *